US011398026B2

United States Patent
Hooper et al.

(10) Patent No.: US 11,398,026 B2
(45) Date of Patent: Jul. 26, 2022

(54) SYSTEMS AND METHODS FOR SYNTHETIC MEDICAL IMAGE GENERATION

(71) Applicant: The Board of Trustees of the Leland Stanford Junior University, Stanford, CA (US)

(72) Inventors: Sarah M. Hooper, Stanford, CA (US); Mirwais Wardak, Stanford, CA (US); Sanjiv S. Gambhir, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 51 days.

(21) Appl. No.: 16/835,060

(22) Filed: Mar. 30, 2020

(65) Prior Publication Data

US 2020/0311932 A1 Oct. 1, 2020

Related U.S. Application Data

(60) Provisional application No. 62/825,714, filed on Mar. 28, 2019.

(51) Int. Cl.
*G06K 9/00* (2022.01)
*G06T 7/00* (2017.01)
(Continued)

(52) U.S. Cl.
CPC ............ *G06T 7/0012* (2013.01); *A61B 6/037* (2013.01); *A61B 6/481* (2013.01); *G06N 3/0454* (2013.01);
(Continued)

(58) Field of Classification Search
CPC .......................... A61B 6/481; G06K 2209/051
See application file for complete search history.

(56) References Cited

U.S. PATENT DOCUMENTS 7,876,938 B2 * 1/2011 Huang ...................... G06T 7/33
382/128
8,915,399 B1 * 12/2014 Nystrom ............ A61K 49/0002
222/63
(Continued)

FOREIGN PATENT DOCUMENTS

WO 2018200493 A1 11/2018

OTHER PUBLICATIONS

"Deep neural networks synthesize full-dose PET images," physicsworld, Retrieved from: https://physicsworld.com/a/deep-neural-networks-synthesize-full-dose-pet-images/, May 22, 2018, 4 pgs.
(Continued)

*Primary Examiner* — Hadi Akhavannik
(74) *Attorney, Agent, or Firm* — KPPB LLP

(57) ABSTRACT

Systems and methods for synthetic medical image generation in accordance with embodiments of the invention are illustrated. One embodiment includes a synthetic medical image generation system, including a processor, and a memory containing an image synthesis application, where the image synthesis application directs the processor to obtain source image data generated by at least one medical imaging device, where the source image data describes a functional medical image taken of a patient administered with a first imaging agent, and synthesize a predicted medical image of the patient that depicts the patient as if they were administered with a second imaging agent, wherein the first imaging agent and the second imaging agent are different imaging agents.

20 Claims, 9 Drawing Sheets

(51) Int. Cl.
| | | |
|---|---|---|
| A61B 6/03 | (2006.01) | |
| A61B 6/00 | (2006.01) | |
| G06N 3/04 | (2006.01) | |
| G16H 50/20 | (2018.01) | |
| G06V 10/40 | (2022.01) | |

(52) U.S. Cl.
CPC ............. *G06V 10/40* (2022.01); *G16H 50/20* (2018.01); *G06T 2207/10104* (2013.01); *G06T 2207/20081* (2013.01); *G06T 2207/20084* (2013.01); *G06T 2207/30016* (2013.01); *G06T 2207/30096* (2013.01)

(56) References Cited

U.S. PATENT DOCUMENTS

| | | | | |
|---|---|---|---|---|
| 9,113,800 | B2* | 8/2015 | Schmidt | A61B 5/415 |
| 2007/0014454 | A1* | 1/2007 | Sawyer | A61N 5/1049 |
| | | | | 382/128 |
| 2008/0057001 | A1* | 3/2008 | Sun | A61K 49/1863 |
| | | | | 424/9.322 |
| 2008/0101665 | A1 | 5/2008 | Collins et al. | |
| 2013/0253319 | A1* | 9/2013 | Hamilton | A61B 5/318 |
| | | | | 600/438 |
| 2015/0072328 | A1* | 3/2015 | Nystrom | A61M 5/14546 |
| | | | | 434/262 |
| 2015/0178916 | A1* | 6/2015 | Sakaguchi | A61B 6/481 |
| | | | | 382/132 |
| 2016/0133037 | A1 | 5/2016 | Vemulapalli et al. | |
| 2016/0210749 | A1 | 7/2016 | Nguyen et al. | |
| 2016/0328846 | A1* | 11/2016 | Trousset | A61B 6/504 |
| 2017/0372497 | A1 | 12/2017 | Hu et al. | |
| 2018/0071452 | A1* | 3/2018 | Sharma | G16H 30/40 |
| 2019/0066493 | A1* | 2/2019 | Sohn | G06K 9/00671 |

OTHER PUBLICATIONS

Bakas et al., "Advancing the Cancer Genome Atlas glioma MRI collections with expert segmentation labels and radiomic features," Scientific Data, Sep. 5, 2017, vol. 4, Article 170117, 13 pgs., doi: 10.1038/sdata.2017.117.

Ben-Cohen et al., "Cross-Modality Synthesis from CT to PET using FCN and GAN Networks for Improved Automated Lesion Detection," arVix, Retrieved from: https://arxiv.org/abs/1802.07846, Jul. 23, 2018, 9 pgs.

Chen et al., "Predicting treatment response of malignant gliomas to bevacizumab and irinotecan by imaging proliferation with [18F] fluorothymidine positron emission tomography: a pilot study," Journal of the American Society of Clinical Oncology, Oct. 20, 2007, vol. 25, No. 30, pp. 4714-21, DOI: 10.1200/JCO.2006.10.5825.

Chen et al., "18F-FDOPA PET Imaging of Brain Tumors: Comparison Study with 18F-FDG PET and Evaluation of Diagnostic Accuracy," Journal of Nuclear Medicine, Jun. 2006, vol. 47, No. 6, pp. 904-911.

Chen et al., "Imaging Proliferation in Brain Tumors with 18F-FLT PET: Comparison with 18F-FDG," Journal of Nuclear Medicine, 2005, vol. 46, pp. 945-952, Jun. 2005;46(6):945-52.

Choi et al., "Generation of Structural MR Images from Amyloid PET: Application to MR-Less Quantification," Journal of Nuclear Medicine, Dec. 7, 2017, 28 pgs.

Glorot et al., "Understanding the difficulty of training deep feedforward neural networks," in the Proceedings of the 13th International Conference on Artificial Intelligence and Statistics, (AISTATS) 2010, Chia Laguna Resort, Sardinia, Italy, vol. 9 of JMLR:W&CP 9, pp. 249-256.

Goodfellow et al., "Generative Adversarial Networks," arXiv, Retrieved from: https://arxiv.org/abs/1406.2661, Jun. 10, 2014, 9 pgs.

Herrman et al., "Comparison of visual and semiquantitative analysis of 18F-FDOPA-PET/CT for recurrence detection in glioblastoma patients," Neuro-Oncology, Apr. 2014, vol. 16. No. 4, pp. 603-609, Advance Access date Dec. 4, 2013, doi:10.1093/neuonc/not166.

Huang et al., "An investigation of a double-tracer technique for positron computerized tomography," Journal of Nuclear Medicine, Sep. 1982, vol. 23, No. 9, pp. 816-822.

Hudson et al., "Accelerated image reconstruction using ordered subsets of projection data," IEEE Transactions on Medical Imaging, Dec. 1994, vol. 13, No. 4, pp. 601-609, doi: 10.1109/42.363108.

Isensee et al., "Brain Tumor Segmentation and Radiomics Survival Prediction: Contribution to the BRATS 2017 Challenge," Computer Science, Computer Vision and Pattern Recognition, arXiv:1802.10508, Feb. 28, 2018.

Isola et al., "Image-to-Image Translation with Conditional Adversarial Networks," arXiv, Retrieved from: https://arXiv.org/abs/1611.07004, Nov. 26, 2018, 17 pgs.

James et al., "A molecular imaging primer: modalities, imaging agents and applications," Physiol. Rev., Apr. 2012, vol. 898-965, pp. 898-965, doi:10.1152/physrev.00049.2010n (Presented in Two Parts).

Kadrmas et al., "Methodology for quantitative rapid multi-tracer PET tumor characterizations," Theranostics, Oct. 4, 2013, vol. 3, No. 10. pp. 757-773, doi: 10.7150/thno.5201.

Kadrmas et al., "Single-scan dual-tracer FLT+FDG PET tumor characterization," NIH Public Access Author Manuscript, published in final edited form as Physics in Medicine and Biology, Feb. 7, 2013, vol. 58, No. 3, pp. 429-449, doi:10.1088/0031-9155/58/3/429.

Koeppe et al., "Dual-[11C]Tracer Single-Acquisition Positron Emission Tomography Studies," Journal of Cerebral Blood Flow & Metabolism, Dec. 1, 2001, vol. 21, pp. 1480-1492, https://doi.org/10.1097/00004647-200112000-00013.

Lecun et al., "Deep Learning," Nature, May 27, 2015, vol. 521, pp. 436-444, doi:10.1038/nature14539.

Lizarraga et al., "18F-FDOPA PET for Differentiating Recurrent or Progressive Brain Metastatic Tumors from Late or Delayed Radiation Injury AfterRadiation Treatment," Journal of Nuclear Medicine, Jan. 1, 2014 vol. 55, No. 1, pp. 30-36, first published Oct. 28, 2013, doi: 10.2967/jnumed.113.121418.

Mao et al., "Lease Squares Generative Adversarial Networks," arXiv e-prints, Submitted Nov. 13, 2016, pp. 2794-2802.

Menze et al., "The Multimodal Brain Tumor Image Segmentation Benchmark (BRATS)," HHS Public Access Author Manuscript, published in final edited for as: IEEE Trans. Med. Imaging, Oct. 2015, vol. 34, No. 10, pp. 1993-2024, doi: 10.1109/TMS.2014.2377694.

Mirza et al., "Conditional Generative Adversarial Nets," arXiv:1411.1784v1 [cs.LG], Nov. 6, 2014, 7 pgs.

Mondal et al., "Few-shot 3D Multi-modal Medical Image Segmentation using Generative Adversarial Learning," arXiv, Retrieved from: https://arxiv.org/abs/1810.12241, Oct. 29, 2018, 10 pgs.

Phelps, "PET: The Merging of Biology and Imaging into Molecular Imaging," Journal of Nuclear Medicine, Apr. 2000, vol. 41, pp. 661-681.

Phelps, "Positron emission tomography provides molecular imaging of biological processes," PNAS, Aug. 1, 2000, vol. 97, No. 16, pp. 9226-9233.

Ronneberger et al., "U-Net: Convolutional Networks for Biomedical Image Segmentation," arXiv, Retrieved from: https://arxiv.org/pdf/1505.04597.pdf, May 18, 2015, 8 pgs.

Schwarzenberg et al., "Treatment Response Evaluation Using 18F-FDOPA PET in Patients with Recurrent Malignant Glioma on Bevacizumab Therapy," Clinical Cancer Research, Jul. 1, 2014, vol. 20, No. 13, pp. 3550-3559, doi:10.11158/1078-0432.CCR-13-1440.

Sikka et al., "MRI to FDG-PET: Cross-Modal Synthesis Using 3D U-Net For Multi-Modal Alzheimer's Classification," 1st Conference on Medical Imaging with Deep Learning (MIDL 2018), Amsterdam, The Netherlands, 2018, 8 pgs.

Wang et al., "3D Conditional Generative Adversarial Networks for High-Quality PET Image Estimation at Low Dose," NeuroImage, vol. 174, Jul. 1, 2018, pp. 550-562.

Wardak et al., "18F-FLT and 18F-FDOPA PET Kinetics in Recurrent Brain Tumors," NIH Public Access Author Manuscript, Published in final edited form as: Eur. J. Nucl. Med. Mol. Imaging, Jun. 2014, vol. 41, No. 6, pp. 1129-1209, doi:10.1007/s00259-013-2678-2.

(56) References Cited

OTHER PUBLICATIONS

Xiang et al., "Deep Embedding Convolutional Neural Network for Synthesizing CT Image from T1-Weighted MR Image," Medical Image Analysis, vol. 47, Jul. 2018, pp. 31-44 (26 pgs.).
Zaharchuk et al., "Deep Learning in Neuroradiology," American Journal of Neuroradiology, Oct. 2018, vol. 39, pp. 1776-1784, doi:10.3174/ajnr.A5543.

\* cited by examiner

SYSTEMS AND METHODS FOR SYNTHETIC MEDICAL IMAGE GENERATION

CROSS-REFERENCE TO RELATED APPLICATIONS

The current application claims priority under 35 U.S.C. § 119(e) to U.S. Provisional Patent Application Ser. No. 62/825,714, entitled "Systems and Methods for Synthetic Medical Image Generation", filed Mar. 28, 2019. The disclosure of U.S. Provisional Patent Application Ser. No. 62/825,714 is hereby incorporated herein by reference in its entirety.

FIELD OF THE INVENTION

The present invention generally relates to systems and methods for generating synthetic medical images, namely the generation of synthetic positron emission tomography (PET) images.

BACKGROUND

A positron emission tomography (PET) scan is a type of nuclear medicine imaging technique in which the patient is administered radioactive materials to non-invasively examine organ and tissue biochemistry in vivo. These radioactive materials, which are radiolabeled or "tagged" with a positron-emitting radionuclide (such as Fluorine-18 or Carbon-11), are sometimes referred to as "tracers," "radiotracers," "radiopharmaceuticals," "molecular imaging probes," "contrast agents," "probes," "agents," or "imaging agents" amongst other terms. In some instances, the radioactive material can be a positron-emitting radionuclide itself. Indeed, there are many different types of imaging agents, regardless of radioactivity, depending upon the imaging modality. For example, microbubbles can be used as imaging agents in ultrasound imaging. There are many types of imaging agents which are used for different medical imaging purposes. PET imaging has been widely adopted as an important research and clinical modality for applications in cancer, cardiovascular disease, infection and neurological disorders.

Magnetic resonance imaging (MRI) scans utilize strong magnetic fields, magnetic field gradients, and radio waves to image a subject. Computed tomography (CT) scans are an additional form of medical imaging technology that uses X-ray measurements taken from different angles to create images. Optical imaging techniques are additional methods that include but are not limited to fluorescence, bioluminescence, and Raman imaging. Medical imaging techniques such as these are useful for non-invasively investigating the internal systems of the human body.

SUMMARY OF THE INVENTION

Systems and methods for synthetic medical image generation in accordance with embodiments of the invention are illustrated. One embodiment includes a synthetic medical image generation system, including a processor, and a memory containing an image synthesis application, where the image synthesis application directs the processor to obtain source image data generated by at least one medical imaging device, where the source image data describes a functional medical image taken of a patient administered with a first imaging agent, and synthesize a predicted medical image of the patient that depicts the patient as if they were administered with a second imaging agent, wherein the first imaging agent and the second imaging agent are different imaging agents.

In another embodiment, the at least one medical imaging device is a positron emission tomography (PET) scanner.

In a further embodiment, the first imaging agent is selected from the group consisting of $^{18}$F-FDOPA, $^{18}$F-FLT, $^{18}$F-MPG, and $^{18}$F-FDG.

In still another embodiment, the second imaging agent is selected from the group consisting of $^{18}$F-FDOPA, $^{18}$F-FLT, $^{18}$F-MPG, and $^{18}$F-FDG.

In a still further embodiment, to synthesize a predicted medical image, the image synthesis application directs the processor to utilize a neural network.

In yet another embodiment, the neural network is a generative adversarial network (GAN), comprising a generator and a discriminator.

In a yet further embodiment, the generator is implemented using a U-Net architecture.

In another additional embodiment, the discriminator is implemented using a PatchGAN architecture capable of processing 3D image volumes.

In a further additional embodiment, the source image data further includes an anatomical image.

In another embodiment again, the image synthesis application further directs the processor to generate at least one mask based on the source image data for use in synthesizing the predicted medical image.

In a further embodiment again, a method for generating synthetic medical images includes obtaining source image data generated by at least one medical imaging device, where the source image data describes a functional medical image taken of a patient administered with a first imaging agent, and synthesizing a predicted medical image of the patient that depicts the patient as if they were administered with a second imaging agent, wherein the first imaging agent and the second imaging agent are different imaging agents.

In still yet another embodiment, the at least one medical imaging device is a positron emission tomography (PET) scanner.

In a still yet further embodiment, the first imaging agent is selected from the group consisting of $^{18}$F-FDOPA, $^{18}$F-FLT, $^{18}$F-MPG, and $^{18}$F-FDG.

In still another additional embodiment, the second imaging agent is selected from the group consisting of $^{18}$F-FDOPA, $^{18}$F-FLT, $^{18}$F-MPG, and $^{18}$F-FDG.

In a still further additional embodiment, synthesizing a predicted medical image comprises utilizing a neural network.

In still another embodiment again, the neural network is a generative adversarial network (GAN), comprising a generator and a discriminator.

In a still further embodiment again, the generator is implemented using a U-Net architecture.

In yet another additional embodiment, the discriminator is implemented using a PatchGAN architecture capable of processing 3D image volumes.

In a yet further additional embodiment, the source image data further includes an anatomical image; and the method further includes generating at least one mask based on the source image data for use in synthesizing the predicted medical image.

In yet another embodiment again, a synthetic medical image generation system includes a processor, and a memory containing an image synthesis application, where the image synthesis application directs the processor to obtain source image data comprising a functional medical image generated by a positron emission tomography (PET) scanner and an anatomical image, where the functional medical image describes a medical image taken of a patient administered with a first imaging agent, where the first imaging agent and the second imaging agent are different imaging agents, co-register the functional medical image with the anatomical image, generate a brain mask based on the anatomical image, generate a tumor mask by extracting features from the anatomical image and the functional medical image scan using a feature extractor neural network, synthesize a predicted medical image of the patient that depicts the patient as if they were administered with a second imaging agent by providing a generative adversarial network (GAN) with the source image data and the tumor mask, where the GAN includes a generator conforming to a U-Net architecture, and a discriminator conforming to a PatchGAN architecture capable of processing 3D image volumes, and provide the predicted medical image via a display.

In a yet further embodiment again, a synthetic medical image generation system includes a processor, and a memory containing an image synthesis application, where the image synthesis application directs the processor to obtain source image data generated by at least one medical imaging device, where the source image data describes a medical image scan taken of a patient administered with a first imaging agent at a first time point, and synthesize a predicted medical image of the patient that depicts the patient as if they were administered with the first imaging agent at a second time point different to the first time point.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings, which form a part of this disclosure.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

DETAILED DESCRIPTION

Figure 1:
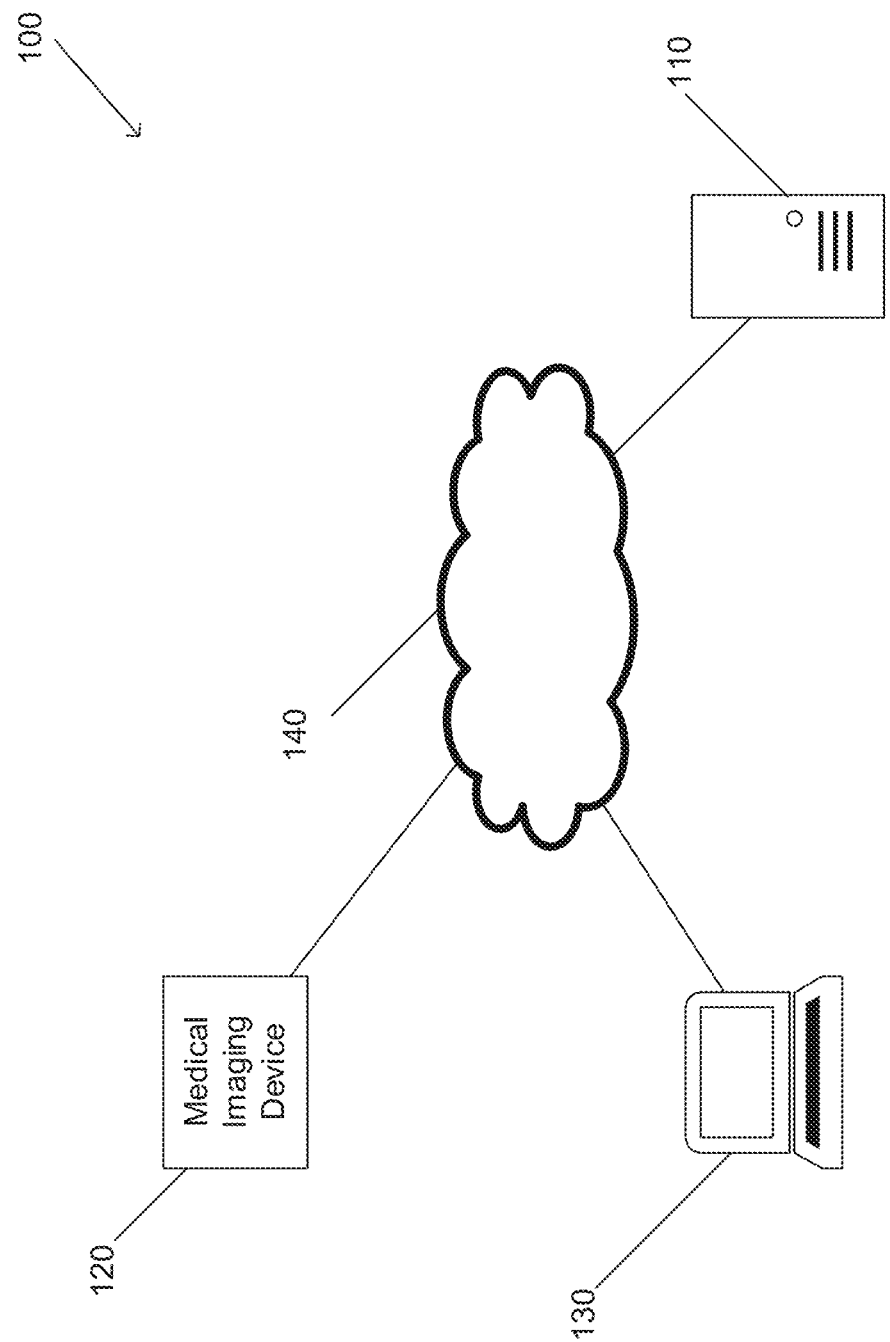
FIG. 1 is a conceptual illustration of a synthetic medical image generation system in accordance with an embodiment of the invention.

Medical imaging techniques that require radioactive imaging agents can be invaluable to medical professionals in diagnosing and otherwise observing the internal systems of their patients on a molecular and biochemical level. However, radionuclide imaging is an ionizing radiation-based modality that delivers a low but non-negligible radiation dose to patients. In addition, the radiation dose to the patient following administration of a PET radiopharmaceutical is directly proportional to the amount of radioactivity administered. Ensuring that diagnostic information is as high as possible while maintaining radiation dose as low as reasonably achievable is an important principle in radiology and nuclear medicine. However, repeat administration of even low doses of radioactive imaging agents can potentially result in accumulated tissue damage over time. Medical professionals sometimes need to administer multiple imaging agents to a single patient because each imaging agent gives different insights into the patient's disease and can guide diagnosis, prognosis, and treatment. For example, the nucleoside imaging agent 3'-deoxy-3'-[$^{18}$F]-fluorothymidine ($^{18}$F-FLT, and interchangeably referred to herein as "FLT") can give information about the DNA synthesis activity of a tumor, while the amino acid analog 3,4-dihydroxy-6-[$^{18}$F]-fluoro-L-phenylalanine ($^{18}$F-FDOPA, and interchangeably referred to herein as "FDOPA") offers insights into the level of amino acid transport into a tumor. It has been previously shown that in patients with malignant glioma on anti-angiogenic therapy, $^{18}$F-FLT PET seems to be more predictive than MRI for early treatment response. Similarly, $^{18}$F-FDOPA PET has proven useful for imaging of recurrent low-grade tumors and for distinguishing tumor recurrence from radiation necrosis. $^{18}$F-FDOPA PET could also assist in better defining tumor margins when planning surgery or radiotherapy. As such, a medical professional investigating a patient's tumor might desire information that requires two or more different types of imaging agents to be injected into a patient. Unfortunately, imaging a patient with multiple radiotracers comes at the expense of increasing the patient's radiation exposure with each additional imaging agent administration. Further, multiple scanning sessions may need to be scheduled, often on different days, resulting in high costs, image alignment issues, potential change in pathophysiology between sessions, and a long and arduous experience for the patient.

Advancements in machine learning have yielded many classes of algorithms, such as the convolutional neural network (CNN) and the generative adversarial network (GAN). CNNs are often utilized to analyze and classify images. A subclass of CNN is the U-Net, which was designed for biomedical image segmentation. The U-Net architecture is described in "U-Net: Convolutional Networks for Biomedical Image Segmentation" by Ronneberger, et al., arXiv:1505.04597, the entirety of which is incorporated by reference herein. GANs are made up of two neural networks which compete with each other to become more accurate in their predictions. The first neural network is a generator, which synthesizes the image. The second neural network is a discriminator, which classifies the true and synthesized images as real or fake and provides feedback to the generator based on the overall quality of the synthesized PET images. The GAN architecture is described in "Generative Adversarial Nets" by Goodfellow, et al., arXiv:1406.2661, the entirety of which is incorporated by reference herein.

Systems and methods described herein can use neural networks to synthesize PET images based on a source PET scan, where the source PET scan was taken of a patient administered with a first imaging agent, and the synthesized PET image is a predicted scan of the organ or body of interest as if the patient had been injected with a second, different imaging agent. In numerous embodiments, the neural networks may include the GAN architecture and the U-Net architecture. In a variety of embodiments, the PET scans (both source and synthesized) are dynamic, and therefore include a series of images collected over time post-imaging agent injection. However, in numerous embodiments, PET scans are a single, static image. As such, "PET scan(s)" and "PET image(s)" are to be understood as equivalent, and can refer to either a static PET image or a dynamic series of PET images. In many embodiments, other medical scans, such as, but not limited to, MRI and CT scans, can be used to augment processes for synthesizing PET scan images.

While previous work has attempted to synthesize PET images using a source medical image (e.g. synthesizing a diagnostic quality, standard full-dose PET image from a low-dose PET image of the same imaging agent), the problem of generating PET images of multiple different imaging agents without having to administer each imaging agent to the subject has not been sufficiently addressed. Other techniques for multi-tracer PET imaging (e.g. using the difference in half-lives of positron-emitting radioisotopes) generally require administration of multiple imaging agents and as a result increase the radiation dose to the subject. Systems and methods described herein address the limitations of prior work using a general framework that synthesizes PET images from existing patient medical imaging scans without increasing radiation dose to the patient, requiring additional imaging sessions, or administration of extra imaging agents. Furthermore, the ability to synthesize and simulate images of different imaging agents can get data to medical professionals more quickly, as the patient does not need to be scanned or administered an imaging agent a second time. Additionally, patients do not necessarily need to be human, and systems and methods described herein can be utilized on non-human subjects as well. Systems and methods described herein enable a new way forward with molecular imaging studies in general, so that multiple targets can be interrogated without having to inject molecular imaging agents for each and every target. Synthetic medical image generation systems are discussed below.

Synthetic Medical Image Generation Systems

Turning now to the drawings, systems and methods for synthetic medical image generation are described. A synthetic medical image generation system in accordance with an embodiment of the invention is illustrated in FIG. 1. System 100 includes a synthetic medical image generation processing system 110. Synthetic medical image generation processing systems are capable of performing synthetic medical image generation processes. Synthetic medical image generation processing systems can be implemented using any of a variety of computing platforms, which is discussed in further detail below. System 100 further includes a medical imaging device 120. Medical imaging devices can be PET scanners (including total-body), MRI scanners, CT scanners, hybrid imaging systems or any other medical imaging method as appropriate to the requirements of specific applications of embodiments of the invention. Medical imaging devices can further include any other device that produces a clinically relevant image or video dataset. Medical imaging devices, depending on their modalities, can capture functional and/or structural images. Functional images refer to those which reflect physiological processes occurring (often via an imaging agent), whereas anatomical (or "structural") images merely show anatomical features. Further, functional or anatomical images may include multiple different images, three dimensional volumes, time-series, and/or any other image structure depending on the design of the particular medical imaging device. In some embodiments, multiple different medical imaging devices are utilized by the system.

System 100 further includes a display device 130. Display devices can display visual information to users, and can be implemented using any number of different display technologies, including, but not limited to, tablet computers, monitors, smartphones, televisions, virtual reality displays, augmented reality displays, mixed reality displays, and/or any other display device as appropriate to the requirements of specific applications of embodiments of the invention. In numerous embodiments, display devices enable inputs from users to synthetic medical image generation processing systems. In a variety of embodiments, display devices and synthetic medical image generation processing systems are implemented using the same hardware.

System 100 further includes a network 140. Networks can be any type of network capable of passing data between systems and devices. Networks can include one or multiple different types of network protocols. In some embodiments, the network is wireless. In a variety of embodiments, the network is wired. In a variety of embodiments, the network includes both wired and wireless components. In numerous embodiments, the network is the Internet. However, the network can be a local area network, a wide area network, an intranet, or any other network type as appropriate to the requirements of specific applications of embodiments of the invention. Network 140 enables the passage of data between medical imaging devices, synthetic medical image generation processing systems, and display devices, as well as any other device connected to the network as appropriate to the requirements of specific applications of embodiments of the invention.

While a specific system is described with respect to FIG. 1, any number of different system architectures can be utilized as appropriate to the requirements of specific applications of embodiments of the invention. A discussion of synthetic medical image generation processing systems is found below.

Synthetic Medical Image Generation Processing Systems

Synthetic medical image generation processing systems can perform synthetic medical image generation processes. In numerous embodiments, synthetic medical image generation processing systems are computing platforms capable of executing machine readable instructions.

Figure 2:
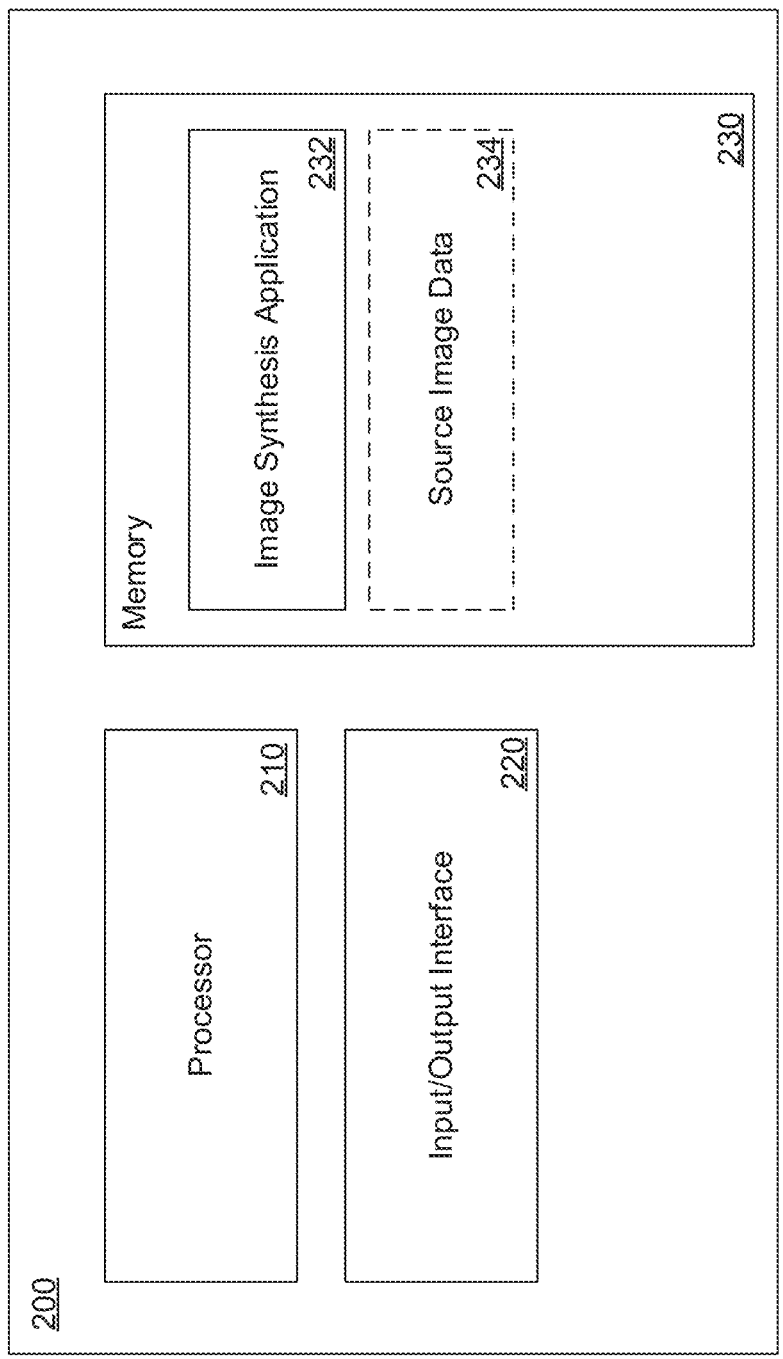
FIG. 2 is a conceptual block diagram of a synthetic medical image generation computing system in accordance with an embodiment of the invention.

Turning now to FIG. 2, a synthetic medical image generation processing system in accordance with an embodiment of the invention is illustrated. Processing system 200 includes a processor 210. Processor 210 can be any logical processing circuitry, including, but not limited to, a central processing unit (CPU), a graphics processing unit (GPU), a field-programmable gate array (FPGA), an application-specific integrated circuit (ASIC), or any other processing component as appropriate to the requirements of specific applications of embodiments of the invention. In numerous embodiments, multiple different processing architectures are used in combination. Processing system 200 further includes an input/output (I/O) interface 220. I/O interfaces can enable communication between the processing system and other components of the synthetic medical image generation system. In numerous embodiments, the I/O interface enables wireless and/or wired connections. In a variety of embodiments, the I/O interface enables communications between different components of the processing system.

Processing system 200 further includes a memory 230. Memory can be implemented using any of a variety of storage devices, including, but not limited to, random access memory (RAM), hard disk drives, solid state drives, and/or any other type of volatile and/or non-volatile memory. Memory 230 stores an image synthesis application 232. Image synthesis applications can direct processors to perform synthetic medical image generation processes. In numerous embodiments, memory 230 further stores source image data 234. Source image data can be any image data obtained from a medical imaging device.

Although a specific architecture for a synthetic medical image generation processing system in accordance with an embodiment of the invention is illustrated in FIG. 2, any number of different architectures can be used as appropriate to the requirements of specific applications of embodiments of the invention. A discussion of synthetic medical image generation processes follows.

Synthetic Medical Image Generation Processes

Synthetic medical image generation processes can obtain source images of a patient from a PET scanner, where the patient was administered with a first imaging agent, and generate a realistic synthetic PET image which reflects what a true PET scan of the patient would look like if they had been administered a different imaging agent. In numerous embodiments, a GAN is utilized to generate the synthetic images after being trained on a set of training images. In a variety of embodiments, additional scans, such as, but not limited to, structural scans (e.g. MRI or CT scans), can be used by synthetic medical image generation processes to increase fidelity of the synthesized image.

Figure 3:
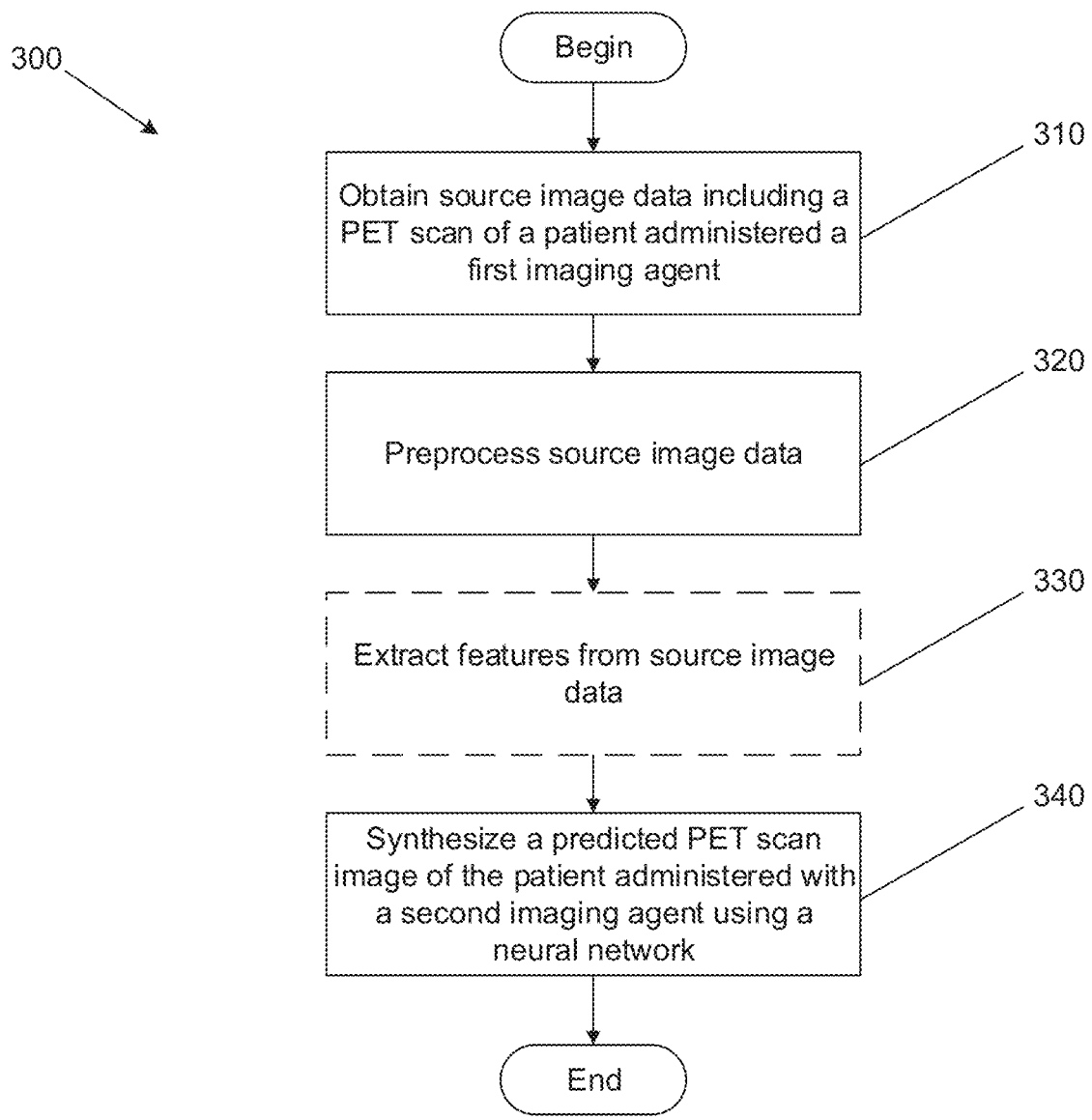
FIG. 3 is a flow chart for a synthetic medical image generation process in accordance with an embodiment of the invention.

Turning now to FIG. 3, a flow chart for how to build a synthetic medical image generation process in accordance with an embodiment of the invention is illustrated. Process 300 includes obtaining (310) source scan data describing a functional static or dynamic PET scan of a patient administered with a first imaging agent. In many embodiments, a structural scan of the patient (e.g. using MR or CT) is also obtained. Process 300 further includes pre-processing (320) the source image data. In numerous embodiments, PET scans described are summed over a pre-determined window of time after administration of the imaging agent to the patient. In numerous embodiments, the window is specific to the type of imaging agent used. Dynamic PET images along with the blood and tissue time-activity curves can also be used. In a variety of embodiments, the MR image is resliced and resized to the same image space as the PET images. The PET and MR images can be co-registered using any number of different co-registration techniques as appropriate to the requirements of specific applications of embodiments of the invention.

Further, in many embodiments, a brain mask can be computed from the MRI or CT data and applied to the PET data. Because PET intensity values vary between patients depending on variables such as injected dose and body weight, and MRI values vary between different scanners and scanning protocols, in various embodiments, each masked image is normalized to the range [0, 1] with 0 representing the non-brain region. In some embodiments, the mean and standard deviation of the brain region are computed for each image type over all training images; the corresponding mean is subtracted from each image and the result is divided by the corresponding standard deviation. In numerous embodiments, each image is cropped such that one voxel separates the brain and the edges of the image. While specific steps for preprocessing data are discussed above, any number of preprocessing steps, including those that use more or fewer preprocessing steps can be utilized as appropriate to the requirements of specific applications of embodiments of the invention.

In various embodiments, process 300 further includes extracting (330) features. In numerous embodiments, the feature extraction step is used to identify relevant structures in the anatomical image and/or imaging agent kinetic information from a dynamic PET scan. In numerous embodiments, the feature extraction can be achieved using a neural network. In some embodiments, feature extraction can be combined with the synthesis network instead of performed separately. In numerous embodiments, the extracted features constitute or are used in the generation of a tumor mask. As can be readily appreciated, masks can be generated without using a neural network using other algorithmic processes, and/or by user input.

In many embodiments, the feature extraction neural network is similar to a U-Net architecture, but with additional short-range concatenations as described in "Brain tumor segmentation and radiomics survival prediction: contribution to the BRATS 2017 challenge." by Isensee, et al., arXiv:1802.10508, the entirety of which is incorporated by reference herein. In a variety of embodiments, the modified U-Net feature extractor is trained to segment gadolinium enhancing tumors by minimizing the Dice loss, given by:

$$L_{Dice} = -2 \frac{\sum_i l_i \hat{l}_i}{\sum_i l_i + \sum_i \hat{l}_i}$$

where, $l_i$ is the true label and $\hat{l}_i$ is the predicted label output from the final sigmoid layer in the network for each voxel i. Once trained, the weights of the feature extractor can be frozen and utilized in conjunction with the GAN architecture as discussed below.

Process 300 further includes synthesizing (340) a PET scan image of the patient using a neural network such that it appears that the patient was administered a second imaging agent. Once trained, the neural network can accept an input stack (e.g. PET scan data, MRI data, and a tumor mask), and output a synthetic PET scan. In numerous embodiments, the neural network is a conditional GAN (cGAN), which learns a mapping from an input image x and a random noise vector z to an output image y. cGANs consist of two networks, a generator (G) and a discriminator (D), pitted against one another in training. In numerous embodiments, the generator's task is to generate a synthetic image ŷ from x and z so that the discriminator cannot distinguish ŷ from the real image y. In a variety of embodiments, the discriminator's adversarial task is to correctly classify y as "real" and ŷ as "fake", where y and ŷ are both conditioned on x. By defining the cGAN loss $L_{cGAN}$ as the discriminator's ability to correctly classify synthetic versus real images, the adversarial loss can be expressed as the min-max optimization:

$$\min_G \max_D L_{cGAN}(G, D)$$

where $L_{cGAN}$ is classically given by the binary cross entropy loss:

$$L_{cGAN}(G,D) = \mathbb{E}_{x,y}[\log D(x,y)] + \mathbb{E}_{x,z}[\log(1-D(x,G(x,z)))]$$

In many embodiments, the cGAN is trained to minimize the least squares loss of both G and D, instead of solving the min-max optimization of the binary cross entropy loss. However, in numerous embodiments, alternative methods, including solving the min-max optimization, can be utilized as appropriate to the requirements of specific applications of embodiments of the invention. Further, in a variety of embodiments, random noise can be introduced into the network via many dropout layers instead of directly adding a noise vector z. In this case, the cGAN loss optimized with the generator and discriminator can be given by:

$$\min_D L_{cGAN}(D) = \frac{1}{2}\mathbb{E}_{x,y}[(D(x,y)-b)^2] + \frac{1}{2}\mathbb{E}_{x,z}[(D(x,G(x,z))-a)^2]$$

$$\min_G L_{cGAN}(G) = \frac{1}{2}\mathbb{E}_{x,z}[(D(x,G(x,z))-c)^2]$$

where a is the label for fake images, b is the label for real images, and c is the label the generator wanted the synthesized images to be given by the discriminator. In many embodiments, b and c are set to random numbers drawn from the uniform distribution [0, 0.1], and a is set to a random number drawn from the uniform distribution [0.9, 1].

Further, the generator can be encouraged to learn to produce a similar image to ground-truth images in a voxel-wise sense by introducing the L1 loss and gradient loss in the generator's optimization equation:

$$L_{L1} = \mathbb{E}_{x,y,z}[\|(y-G(x,z))\|_1]$$

$$L_{Gd}(G) = \mathbb{E}_{x,y,z}[\|\nabla_x y - \nabla_x G(x,z)\|_1 + \|\nabla_y y - \nabla_y G(x,z)\|_1 + \|\nabla_z y - \nabla_z G(x,z)\|_1]$$

where the gradients can be approximated by convolving the images with 3D Sobel filters. In this way, adding the L1 and gradient loss to the cGAN loss can help ensure the generated images do not deviate significantly from ground truth images, as a low mean absolute error is mathematically maintained.

In light of the above, in numerous embodiments, the discriminator and generator loss functions optimized during training are given, respectively, by:

$$\min_D L_{cGAN}(D) = \frac{1}{2}\mathbb{E}_{x,y}[(D(x,y)-b)^2] + \frac{1}{2}\mathbb{E}_{x,z}[(D(x,G(x,z))-a)^2]$$

$$\min_G L_{cGAN}(G) = \frac{1}{2}\mathbb{E}_{x,z}[(D(x,G(x,z))-c)^2] + \lambda_1 L_{L1}(G) + \lambda_2 L_{Gd}(G)$$

where $\lambda_1$ and $\lambda_2$ are constant hyperparameters.

Figure 4:
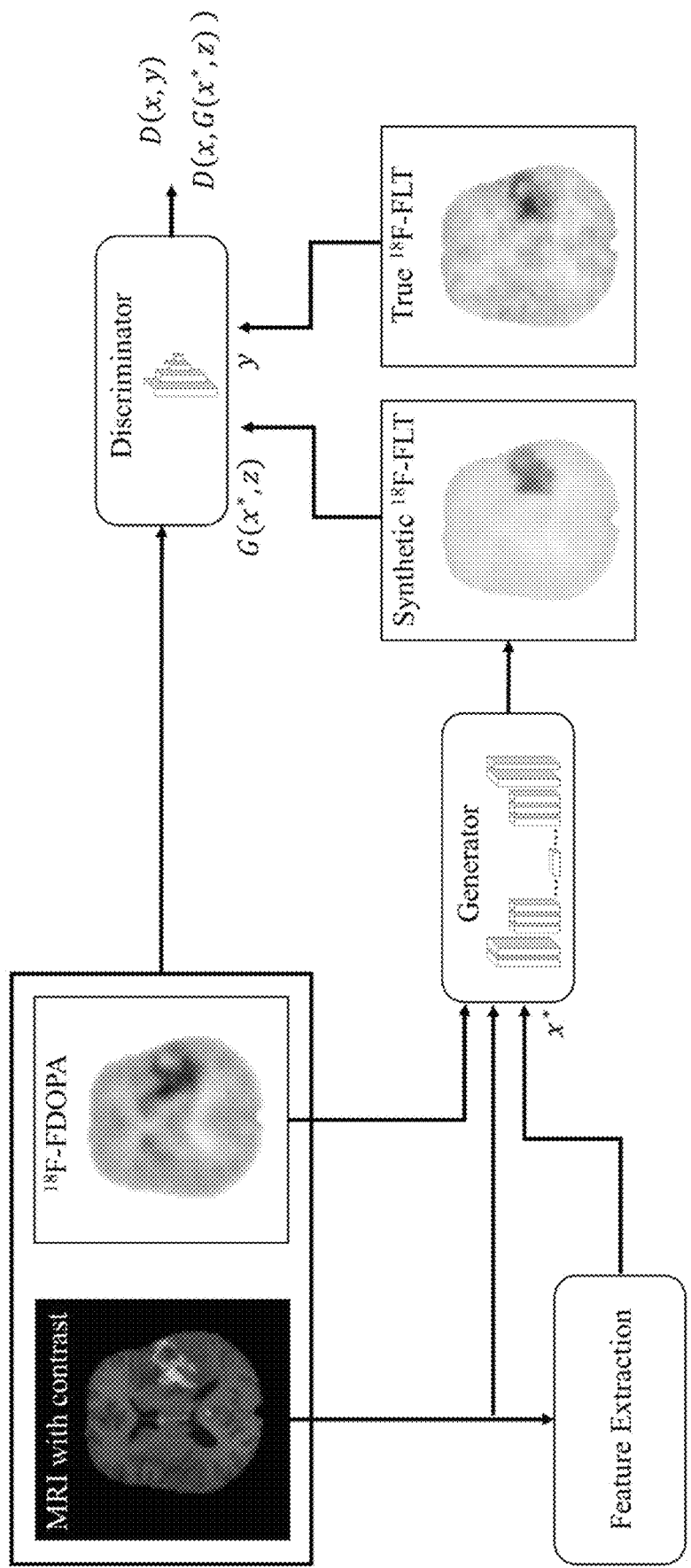
FIG. 4 is a block diagram for a synthetic medical image generation pipeline in accordance with an embodiment of the invention.

With further respect to cGAN architectures, in numerous embodiments, the cGAN's generator architecture also resembles a U-Net architecture. However, unlike the conventional U-Net architecture, the cGAN generator described herein can process three dimensional data to predict entire image volumes. This architecture can be used to progressively downsample and subsequently upsample the input image to produce a high-resolution output image. Since the input and output images are different representations of the same underlying structure (i.e. the patient's brain), long range concatenations can be used to enable low-level information to be shared between the encoder and decoder, incorporating information from different layers of input abstraction into the output image. A block diagram for a synthetic medical image generation pipeline illustrating the feature extractor network and the cGAN in accordance with an embodiment of the invention is illustrated in FIG. 4.

Figure 5:
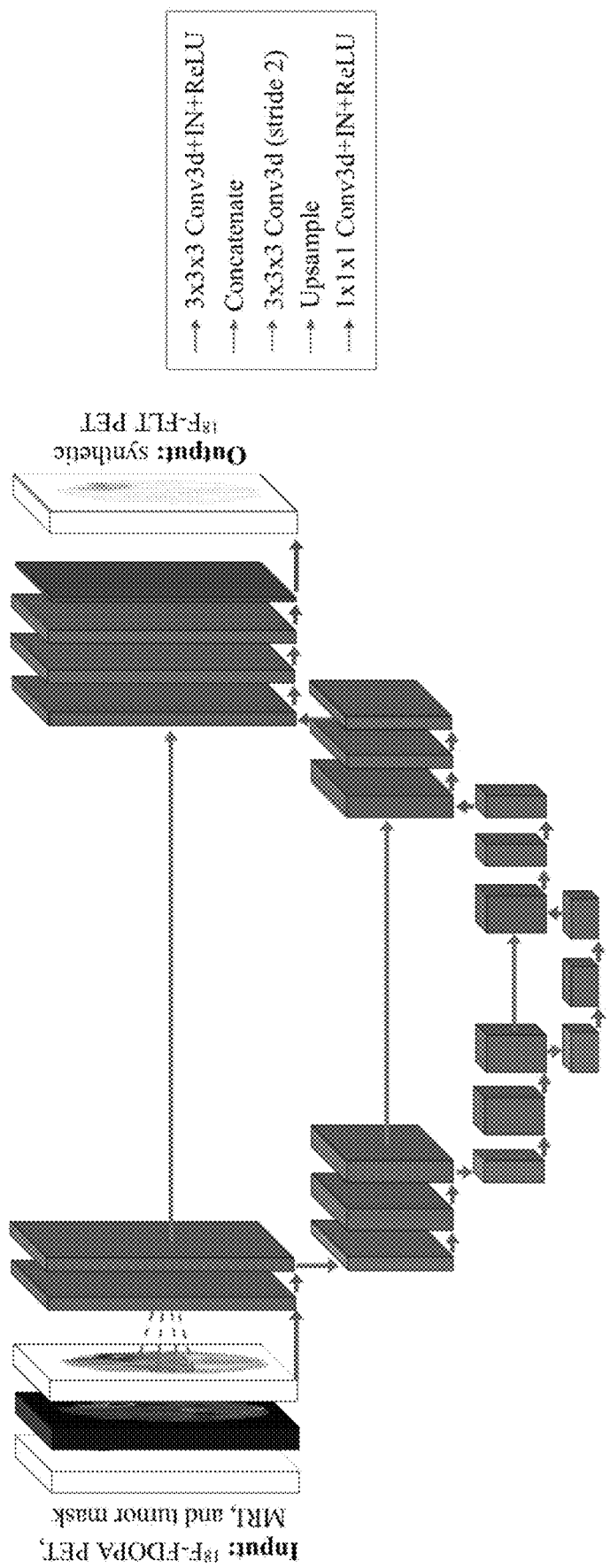
FIG. 5 is a conceptual structural diagram for a generator U-Net architecture in accordance with an embodiment of the invention.

An example of the depth, number of convolutional layers, and number of filters per convolutional layer in the generator are illustrated in accordance with an embodiment of the invention in FIG. 5. In many embodiments, the encoder consists of three pairs of convolutional layers with a stride of one. The convolutional layers in the first pair each have 32 filters, the second pair each have 64 filters, and the third pair each have 128 filters. In a variety of embodiments, after each convolutional layer pair, there is a convolutional layer with a stride of two that preserves the number of feature channels but halves the height, width, and depth of the feature maps.

The decoder can also include three pairs of convolutional layers with a stride of one; the first convolutional layer in each decoder pair quarters the number of channels and the second convolutional layer in each pair maintains the number of channels. In the decoder, each convolutional layer pair can be preceded by interpolation and concatenation operations. The interpolation operation can apply trilinear interpolation to the feature map to increase its height, width, and depth by a factor of two. The interpolated feature map is concatenated with the corresponding feature map from the encoder. The encoder can be connected to the decoder via two convolutional layers that each preserve the number of channels in the feature map. However, one of ordinary skill in the art can appreciate that the number of layers and filters can be modified without departing from the scope or spirit of the invention.

In many embodiments, all convolutional layers in the encoder and decoder can apply 3D convolutions with 3×3×3 kernels and can be followed by instance normalization (IN), rectified linear unit (ReLU) activation, and a dropout layer. Following the final pair of convolutional layers in the decoder, two convolutional layers with 1×1×1 kernels can be appended to produce the output image. The first convolutional layer halves the number of feature channels and the second convolutional layer outputs the final synthetic image. However, any number of different depths, number of convolutional layers, and number of filters can be utilized as appropriate to the requirements of specific applications of embodiments of the invention.

Figure 6:
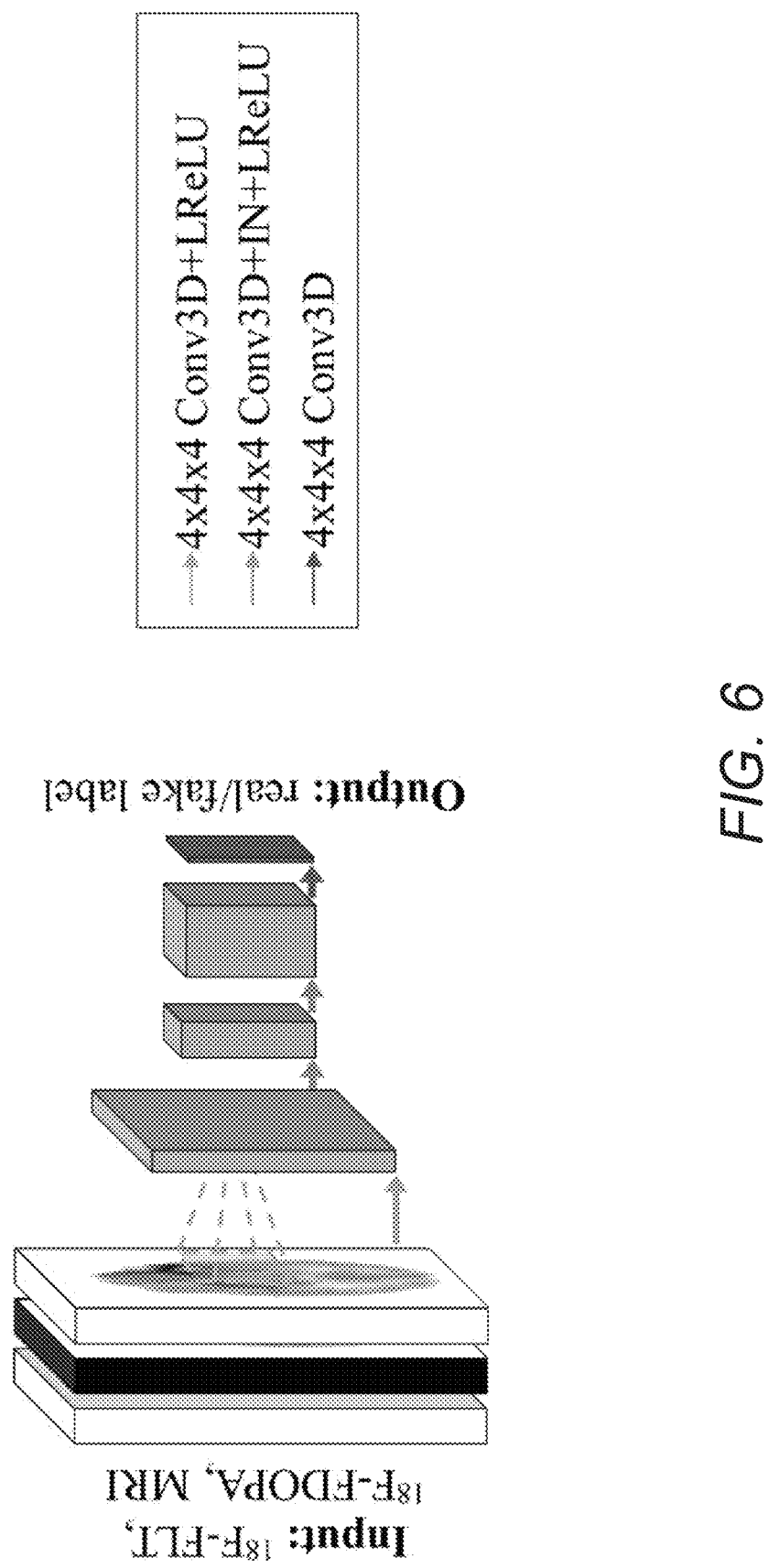
FIG. 6 is a conceptual structural diagram for a discriminator architecture in accordance with an embodiment of the invention.

In numerous embodiments, the discriminator of the cGAN is modeled after the PatchGAN architecture but processes 3D image volumes. Instead of producing a label for the entire image, this approach can produce a label for many patches in the synthesized image to encourage the generator to learn high-frequency information that is often lost when using the L1 distance to optimize the generator. In many embodiments, the discriminator uses four convolutional layers with 64, 128, 256, and one 4×4×4 filters respectively; the first convolutional layer is followed by a leaky ReLU activation while the second and third convolutional layers are each followed by an instance normalization layer and leaky ReLU activation. A discriminator architecture in accordance with an embodiment of the invention is illustrated in FIG. 6

Figure 7:
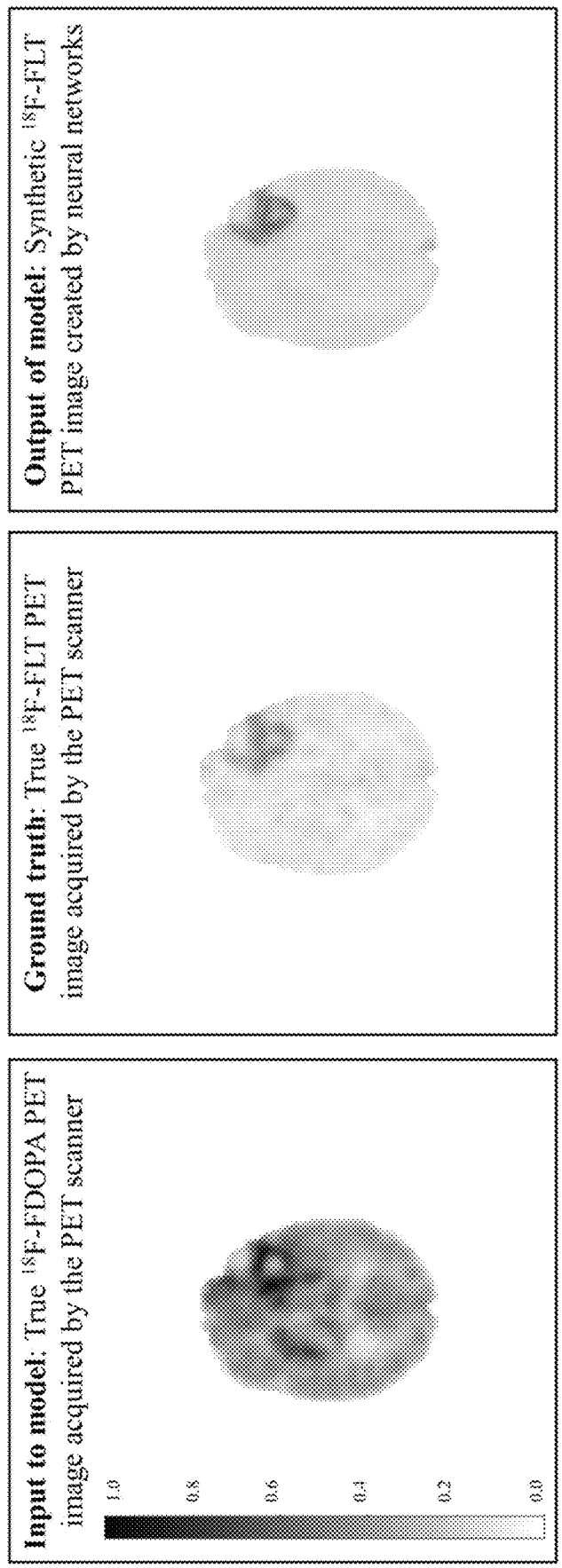
FIG. 7 illustrates an input PET image of $^{18}$F-FDOPA, a ground truth PET image of $^{18}$F-FLT, and a synthesized PET image of $^{18}$F-FLT produced by a synthetic medical image generation process in accordance with an embodiment of the invention.
Figure 8:
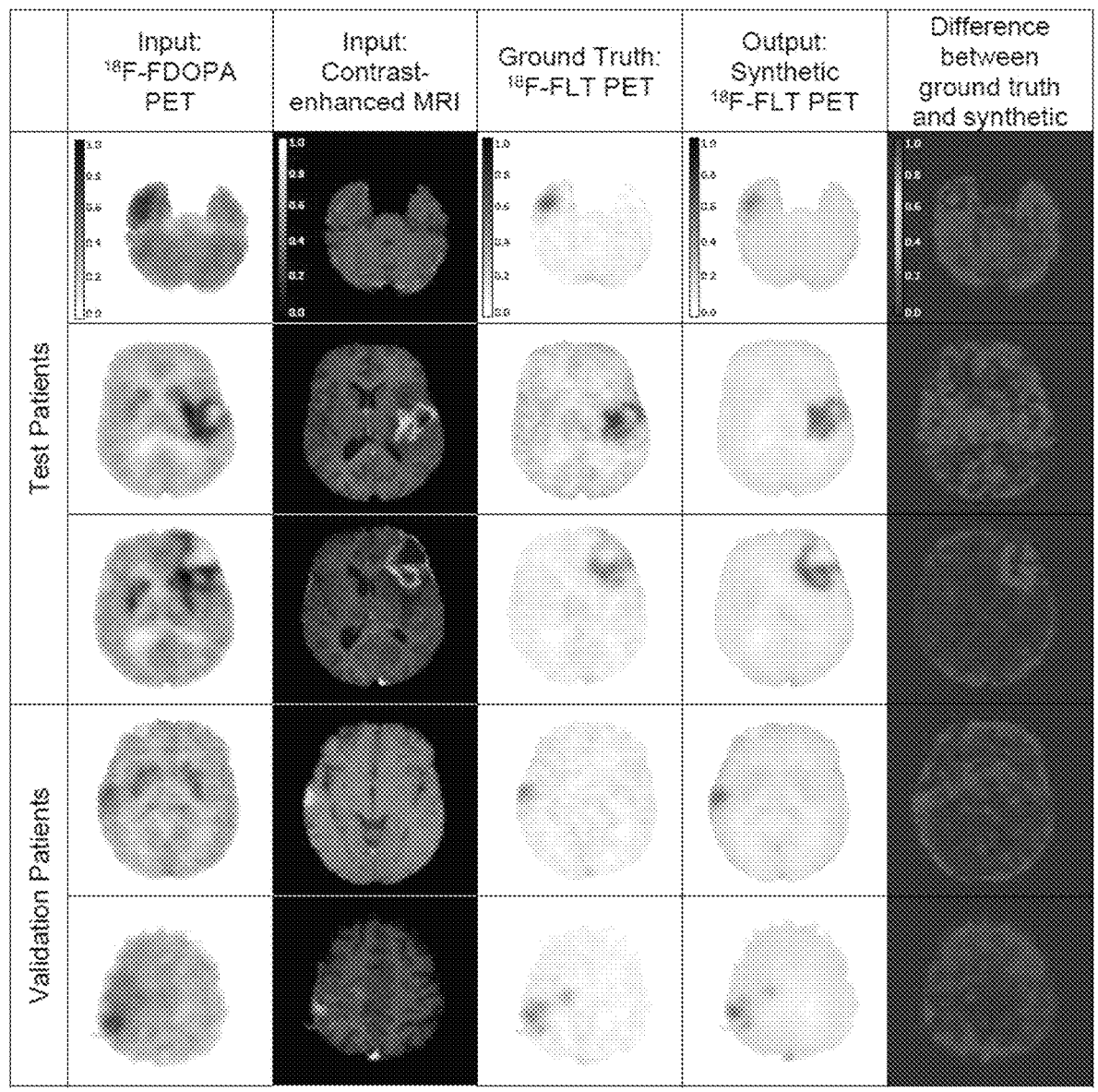
FIG. 8 illustrates ground truth PET scan images of $^{18}$F-FLT and corresponding synthetic PET scan images for five patients produced by a synthetic medical image generation process in accordance with an embodiment of the invention.

An input PET image, a ground truth PET image, and a synthetic PET image made using a synthetic medical image generation process in accordance with an embodiment of the invention is illustrated in FIG. 7. A set of ground truth PET and MR images and corresponding synthetic PET images for five separate patients made using a synthetic medical image generation process in accordance with an embodiment of the invention is illustrated in FIG. 8.

Figure 9:
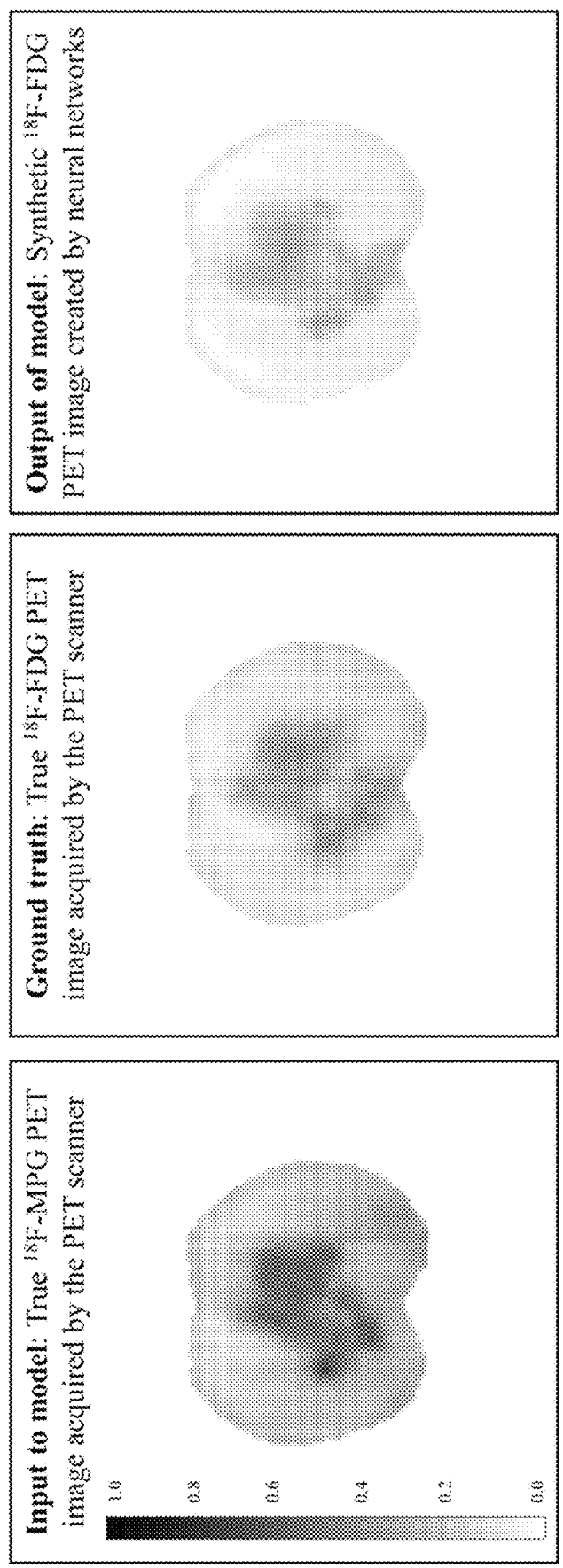
FIG. 9 illustrates an input image of $^{18}$F-MPG, a ground truth image of $^{18}$F-FDG, and a synthesized image of $^{18}$F-FDG produced by a synthetic medical image generation process in accordance with an embodiment of the invention.

As described above, trained neural networks can be used to generate synthetic PET scan images. While generating synthetic $^{18}$F-FLT PET images from input $^{18}$F-FDOPA PET images is discussed above, it is appreciated that any number of different trainings can be similarly performed to enable other types of synthetic images representing different imaging agents. Further, while the above discusses systems and methods applied to brain scans, scans of other organs (e.g. the heart, lungs, or whole body) and tissues can be equally utilized. For example, the same image synthesis system has been used to generate preliminary results of synthetic $^{18}$F-FDG PET images from $^{18}$F-MPG PET/CT scans of patients with lung cancer. $^{18}$F-FDG and $^{18}$F-MPG are also known by their full chemical names, 2-deoxy-2-[$^{18}$F]fluoro-D-glucose and N-(3-chloro-4-fluorophenyl)-7-(2-(2-(2-(2-$^{18}$F-fluoroethoxy) ethoxy) ethoxy) ethoxy)-6-methoxyquinazolin-4-amine, respectively. A set of ground truth $^{18}$F-FDG and $^{18}$F-MPG PET images along with a synthetic $^{18}$F-FDG PET image generated in accordance with an embodiment of the invention is shown in FIG. 9.

Although specific methods of medical image synthesis are discussed above, many different methods including, but not limited to, those that utilize different training data sets, altered neural network parameters, and/or merged architectures, can be implemented in accordance with many different embodiments of the invention. For example, in numerous embodiments, the feature extraction neural network and the synthesis neural network can be combined, meaning that the separate feature extraction network can be excluded. This includes adapting the neural network architecture to take more than one molecular imaging scan and/or output more than one imaging scan, thus generalizing the system into an N-input→M-output imaging agent mapping where N and M can each be larger than one.

Additionally, while embodiments utilizing CNNs and GANs are discussed above, many other machine learning architectures or combinations of architectures may be used instead. Examples of these architectures include, but are not limited to, fully connected neural networks, recursive neural networks, probabilistic neural networks, residual neural networks, CycleGANs, dynamic neural networks, and modular neural networks.

Furthermore, systems and methods described herein can provide a generalized and robust deep learning framework that can be applied to additional applications where synthesizing new molecular imaging scans using pre-existing images is needed. For instance, systems and methods described herein can be applied to take a PET image acquired at an early time point and generate a synthetic PET image of the same imaging agent at a later time point post-injection. Alternatively, one could acquire a PET image at a late time point and generate a synthetic image at an early time point. These approaches could be particularly useful for peptide and antibody imaging agents but is not limited to this class of imaging agents.

In some embodiments, PET images can be synthesized to predict therapy or drug response. For instance, synthesizing a PET image of a future clinical state using a baseline PET scan acquired before therapeutic intervention can potentially assist in therapy planning, predicting response to therapy, and prognosis. Moreover, in many embodiments, systems and methods described herein may be used to take PET scan images acquired after administering a patient with multiple PET imaging agents (sequentially or simultaneously) and synthesize PET images as if each imaging agent had been administered separately during different imaging sessions. Furthermore, in numerous embodiments, scans of a patient in one modality (e.g. PET) can be used to synthesize an image of another modality (e.g. CT, MR or optical). While many embodiments are discussed above with reference to PET images, systems and methods described herein can be extended to other imaging modalities, including optical imaging, CT, MRI, functional MRI, single-photon emission computed tomography (SPECT), photoacoustic imaging, mass spectrometry imaging, digital histopathology, hyperpolarized MRI and ultrasound.

It is therefore to be understood that the present invention may be practiced in ways other than specifically described, without departing from the scope and spirit of the present invention. Thus, embodiments of the present invention should be considered in all respects as illustrative and not restrictive. Accordingly, the scope of the invention should be determined not by the embodiments illustrated, but by the appended claims and their equivalents.

What is claimed is:

1. A synthetic medical image generation system, comprising:
   a processor; and
   a memory containing an image synthesis application, where the image synthesis application directs the processor to:
      obtain source image data generated by at least one medical imaging device, where the source image data describes a medical image taken of a patient administered with a first real chemical imaging agent; and
      synthesize a predicted medical image of the patient based on the source image data, where the predicted medical image depicts the patient as if they were administered with a second real chemical imaging agent, wherein the first real chemical imaging agent and the second real chemical imaging agent are different real chemical imaging agents.

2. The system of claim 1, wherein the at least one medical imaging device is a positron emission tomography (PET) scanner.

3. The system of claim 1, wherein the first real chemical imaging agent is selected from the group consisting of $^{18}$F-FDOPA, $^{18}$F-FLT, $^{18}$F-MPG, and $^{18}$F-FDG.

4. The system of claim 1, wherein the second real chemical imaging agent is selected from the group consisting of $^{18}$F-FDOPA, $^{18}$F-FLT, $^{18}$F-MPG, and $^{18}$F-FDG.

5. The system of claim 1, wherein to synthesize a predicted medical image, the image synthesis application directs the processer to utilize a neural network.

6. The system of claim 5, wherein the neural network is a generative adversarial network (GAN), comprising a generator and a discriminator.

7. The system of claim 6, wherein the generator is implemented using a U-Net architecture.

8. The system of claim 6, wherein the discriminator is implemented using a PatchGAN architecture capable of processing 3D image volumes.

9. The system of claim 1, wherein the source image data further comprises an anatomical image.

10. The system of claim 1, wherein the image synthesis application further directs the processor to generate at least one mask based on the source image data for use in synthesizing the predicted medical image.

11. A method for generating synthetic medical images, comprising:
   obtaining source image data generated by at least one medical imaging device, where the source image data describes a medical image taken of a patient administered with a first real chemical imaging agent; and
   synthesizing a predicted medical image of the patient based on the source image data, where the predicted medical image depicts the patient as if they were administered with a second real chemical imaging agent, wherein the first real chemical imaging agent and the second real chemical imaging agent are different real chemical imaging agents.

12. The method of claim 11, wherein the at least one medical imaging device is a positron emission tomography (PET) scanner.

13. The method of claim 11, wherein the first real chemical imaging agent is selected from the group consisting of $^{18}$F-FDOPA, $^{18}$F-FLT, $^{18}$F-MPG, and $^{18}$F-FDG.

14. The method of claim 11, wherein the second real chemical imaging agent is selected from the group consisting of $^{18}$F-FDOPA, $^{18}$F-FLT, $^{18}$F-MPG, and $^{18}$F-FDG.

15. The method of claim 11, wherein synthesizing a predicted medical image comprises utilizing a neural network.

16. The method of claim 15, wherein the neural network is a generative adversarial network (GAN), comprising a generator and a discriminator.

17. The method of claim 16, wherein the generator is implemented using a U-Net architecture.

18. The method of claim 16, wherein the discriminator is implemented using a PatchGAN architecture capable of processing 3D image volumes.

19. The method of claim 11, wherein the source image data further comprises an anatomical image; and the method further comprises generating at least one mask based on the source image data for use in synthesizing the predicted medical image.

20. A synthetic medical image generation system, comprising:
   a processor; and
   a memory containing an image synthesis application, where the image synthesis application directs the processor to:
     obtain source image data comprising a functional medical image generated by a positron emission tomography (PET) scanner and an anatomical image, where the functional medical image describes a medical image taken of a patient administered with a first imaging agent, where the first imaging agent and the second imaging agent are different imaging agents;
     co-register the functional medical image with the anatomical image;
     generate a brain mask based on the anatomical image;
     generate a tumor mask by extracting features from the anatomical image and the functional medical image scan using a feature extractor neural network;
     synthesize a predicted medical image of the patient that depicts the patient as if they were administered with a second imaging agent by providing a generative adversarial network (GAN) with the source image data and the tumor mask, where the GAN comprises:
       a generator conforming to a U-Net architecture; and
       a discriminator conforming to a PatchGAN architecture capable of processing 3D image volumes; and
     provide the predicted medical image via a display.

* * * * *